United States Patent [19]

Purdy

[11] 4,006,038
[45] Feb. 1, 1977

[54] HEAT REFLECTING TAPE FOR THERMOELECTRIC CONVERTER

[75] Inventor: David L. Purdy, Indiana, Pa.

[73] Assignee: ARCO Medical Products Company, Leechburg, Pa.

[22] Filed: Nov. 13, 1975

[21] Appl. No.: 631,587

Related U.S. Application Data

[60] Division of Ser. No. 205,591, Dec. 7, 1971, Pat. No. 3,923,551, which is a division of Ser. No. 817,271, April 14, 1969, Pat. No. 3,649,367, which is a continuation of Ser. No. 554,874, June 2, 1966, abandoned.

[52] U.S. Cl. ............................ 136/225; 136/224
[51] Int. Cl.² ........................................ H01L 25/00
[58] Field of Search ........................... 136/224, 225

[56] References Cited
UNITED STATES PATENTS

| | | | |
|---|---|---|---|
| 3,816,182 | 6/1974 | McAdam | 136/225 |
| 3,925,104 | 12/1975 | Thomas | 136/225 |

*Primary Examiner*—Leland A. Sebastian
*Attorney, Agent, or Firm*—John R. Ewbank

[57] ABSTRACT

Threads are interlaced with thermoelectric wires to provide a woven cloth in tape form, there being an intermediate layer of heat radiation reflecting material (e.g., aluminum foil) insulated electrically from said wires, which are of opposite thermoelectric polarity and connected as a plurality of thermocouples.

2 Claims, 17 Drawing Figures

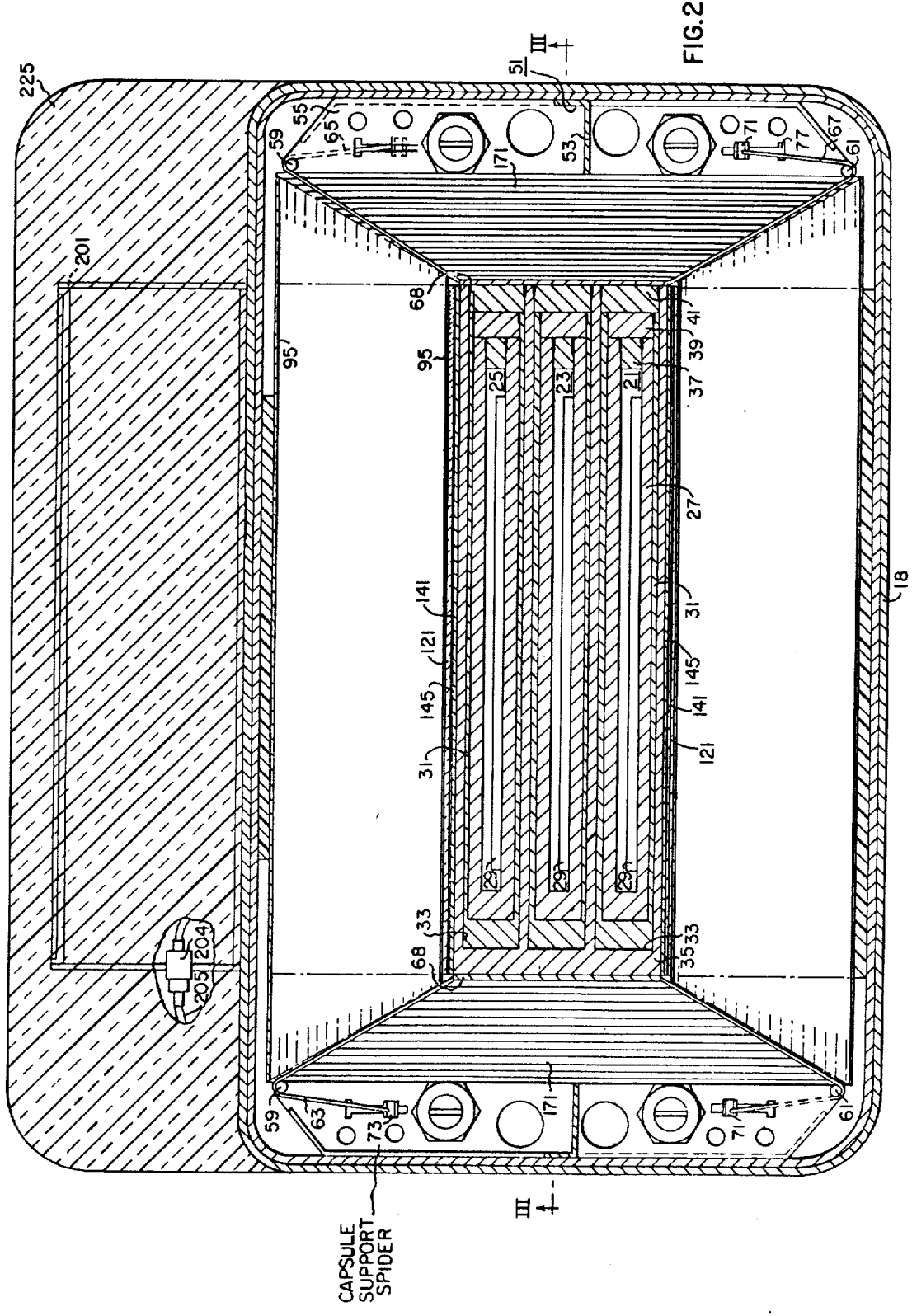

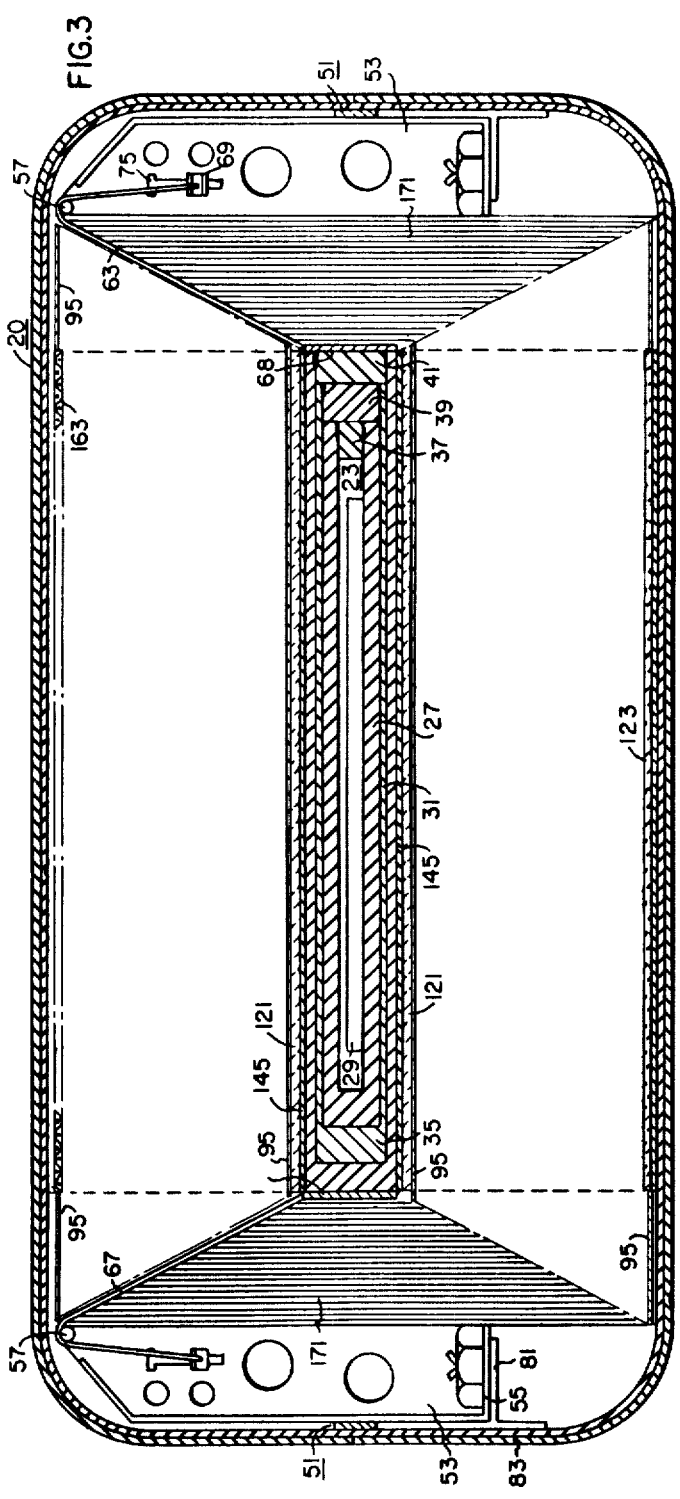
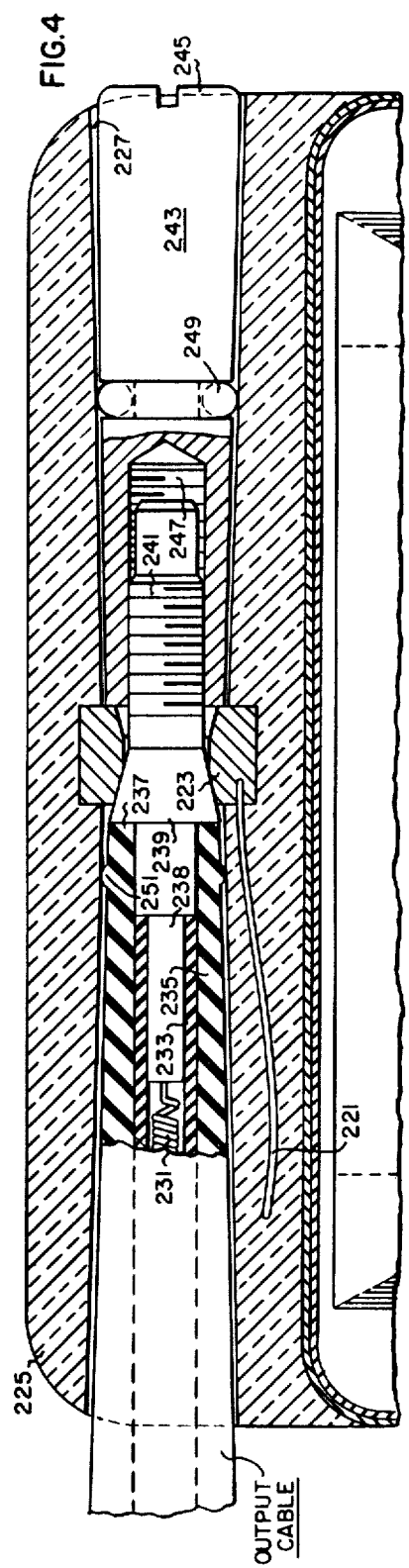

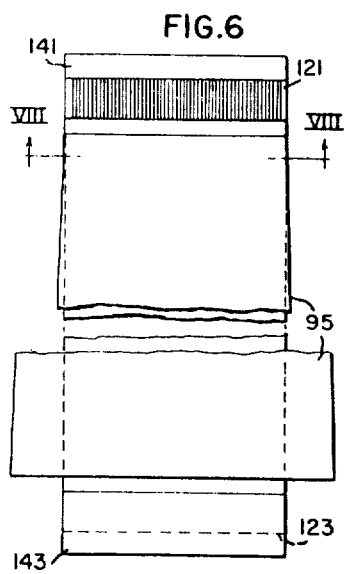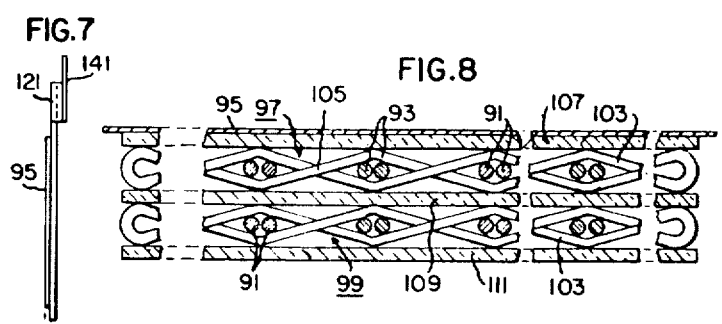

HEAT REFLECTING TAPE FOR THERMOELECTRIC CONVERTER

CROSS REFERENCE TO RELATED APPLICATIONS

This is a division of U.S. Pat. No. 3,923,551 derived from Ser. No. 205,591, filed Dec. 7, 1971, which was a division of U.S. Pat. No. 3,649,367, derived from Ser. No. 817,271, filed April 14, 1969, which was a continuation of Ser. No. 554,874, filed June 2, 1966 now abandoned. U.S. Pat. No. 3,607,443 from Ser. No. 581,506 of Sept. 23, 1966 also benefits from said Ser. No. 554,874.

BACKGROUND OF THE INVENTION

This invention relates to the generation of electrical energy and has particular relationship to completely self-sufficient generators which create electrical energy in places where no other sources than such generators are available. Among the devices for which such a generator can serve as a power supply are cardiac pacemakers or heart pacers.

A heart pacer supplies electrical pulses to the heart of a patient or subject to drive the pumping muscles of the heart. The pacer includes a pulse generator embedded below the abdomen of a subject and an electrode in driving engagement with the heart. The electrode is connected to the generator through a cable. The cathode pole of the pulse supply is at the electrode; the anode pole in the generator. Each pulse is typically a square-wave pulse having a duration of about 1.5 milliseconds. Typically the pulse current is between 4 and 10 milliamperes; the load supplied by the pulses is 300 to 700 ohms paralleled by a capacitance of 0.25 microfarads and resistance of 1000 ohms. The frequency of the pulses depends on the subject and typically is 70 plus or minus 5 per minute for humans and 12.0 plus or minus 5 per minute for dogs. The generator should deliver a voltage of about 6 volts. The installation of a pacer in a subject demands major surgery.

In pacemakers in accordance with the teachings of the prior art the supply is a battery of long-life cells, such as MERCURY cells. But the life of such a battery is at most two or three years and in the light of the danger to the subject of loss of battery power and the surgery required to replace batteries a much longer-life power supply is required. To overcome this disadvantage of the prior art, a generator is provided which includes a central radioactive fuel capsule about which is wound spirally, fabric having embedded therein strands of thermocouple material. Foil of heat radiation reflecting material and of insulation are wound between the layers of fabric. Typically, the fabric may be formed by spinning thermal insulating thread, for example quartz thread, as woof on the thermoelectric strands as warp. The thread may be the warp and the thermoelectric strands the woof but this has the disadvantage that the relatively stiff metal strands must be turned under and over the yieldable quartz thread rather than the converse. Alternate thermoelectric strands are of opposite polarity materials and the ends of adjacent strands are conductively joined so that the opposite-polarity strands of the tape form a thermopile of long thermocouples in series.

The tape is wound so that the ends of the thermoelectric strand on the inside of the spiral are contiguous to the capsule and form the hot junction of the pile. The ends of the tape on the outside of the spiral form the cold junction.

To achieve the desired voltage which may be as high as six volts, it is necessary that a large number of thermocouples of the wires in the tape be connected in series and for this purpose it is necessary that the hot and cold junctions be formed of the wire ends of wires of opposite thermoelectric polarity. In these junctions the wire ends must be joined in firm electrical contact and the junctions must be effectively insulated from each other. It is an object of this invention to achieve this desideration; that is, to provide an electrical component including sets of wires having terminal ends to be joined in firm electrical contact with the joined terminal ends of different sets of the wires effectively insulated from each other.

SUMMARY OF THE INVENTION

In accordance with this invention, there are provided ceramic tabs having grooves. Each groove has a coating of a metal which adheres to the ceramics, the coatings in different grooves being separated and insulated from each other. Brazing metal, for example copper and silver, is deposited on the coating in each groove and the wire ends of the different sets of wires are fused in by the brazing metal and are joined in firm electrical contact.

There is also provided in accordance with this invention a thermoelectric tape with heat-radiation reflecting material over its surface.

The generator according to this invention has the following advantages:

1. Optimum ratio of thermocouple length to diameter; the thermal conduction path is then long assuring maximum temperature difference, at the same time there is adequate internal power attenuation not subject to short-circuits.
2. Ruggedness and capability of resistance to shock.
3. Minimum space geometry; that is, small dimensions.
4. Adaptability to large scale mechanized production and testing.

Typically, Cupron Special and Tophel Special thermocouple strands may be included in the tape and they may be connected in parallel redundancy for optimum reliability. Cupron Special is a copper-nickel-manganese alloy, typically 59.5% Cu, 40% Ni, 0.5 Mn; Tophel Special is a copper-nickel alloy typically 90% Cu, 10% Ni. The strands spiral from the central fuel source and occupy the space between the radiation foil vacuum insulation. The thermocouples are attached to the capsule at one end and the heat rejection sink which is the container exterior at the other. The thermocouples are woven as the lengthwise fibers into quartz cloth and are electrically insulated from each other by the laterally woven quartz fibers. This construction combines excellent insulating properties with shock and vibration support. Typically, an external case of titanium, selected for its inertness to body fluids as well as its favorable strength-to-weight ratio, hermetically encloses the bundle formed by the central fuel core and the spirally wound thermocouple ribbons with their interleaved radiation shields. In making the generator the case with its contents is sealed by electron-beam welding in a high vacuum. The power leads are brought, typically, through alumina ceramic-to-metal seals into another hermetically sealed chamber containing the heart pacer pulser. Another ceramic-tometal seal conducts the signal to a terminal sealed in clear epoxy. This epoxy is transparent so that the surgeon has a clear view to assure the final connection of the heart lead to the terminal.

All components of the generator made in the practice of this invention are ceramic or metal. To avoid degradation of the vacuum, organic materials are not used within the titanium envelope. The materials from which the radiation shields are made are self-gettering and the vacuum, rather than to degrade, improves over the life of the unit. Connections are made with high conductivity copper conductor straps, as well as extremely low-heat fluxes to minimize the temperature gradients. Typically a generator according to this invention with the pulser can be constructed to fit within a 2.8 × 5 × 6 centimeter envelope.

BRIEF DESCRIPTION OF DRAWINGS

For a better understanding of this invention, both as to its organization and as to its method of operation, together with additional objects and advantages thereof, reference is made to the following description, taken in connection with the drawings, in which:

FIG. 2 is a view in section taken along line II—II of FIG. 1;

FIG. 3 is a view in section taken along line III—III of FIG. 2;

FIG. 4 is a view in section taken along line IV—IV of FIG. 1;

FIG. 6 is a plan view of the tape of the apparatus shown in FIGS. 1 through 5;

FIG. 7 is a view in end elevation of this tape;

FIG. 8 is an enlarged view in section taken along line VIII—VIII of FIG. 6;

FIG. 9 is an enlarged diagrammatic view of the tape showing how the thermoelectric strands are connected;

FIG. 10 is a plan view enlarged of an end tab to which the thermoelectric strands are connected;

FIG. 11 is a view in side elevation enlarged of this end tab;

FIG. 12 is a view in end elevation enlarged of this end tab;

FIGS. 13A and 13B are plan views enlarged of a single groove of an end tab showing how the ends of the thermoelectric strands are connected in the grooves of the end tabs;

FIGS. 14A and 14B are views in end elevation of the structures shown in FIGS. 13A and 13B; and FIG. 15 is a schematic of apparatus according to this invention.

DETAILED DESCRIPTION OF EMBODIMENT

Figure 1:
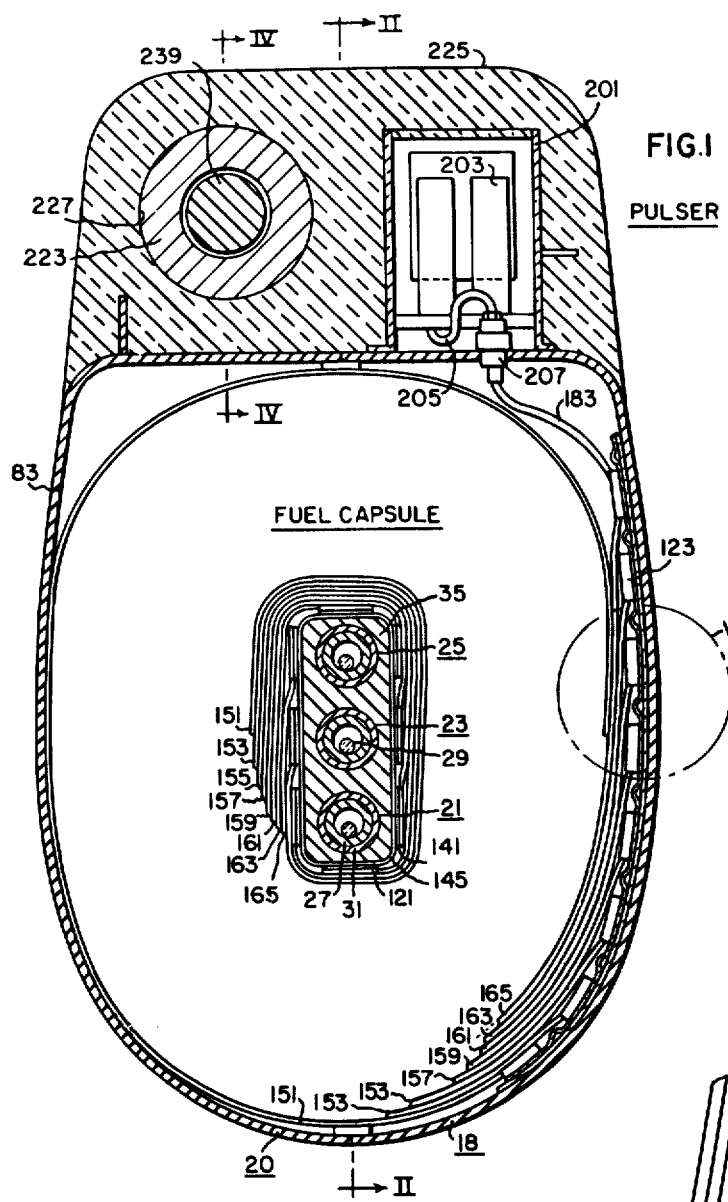
FIG. 1 is a view in transverse section of a heart pacer according to this invention.
Figure 5:
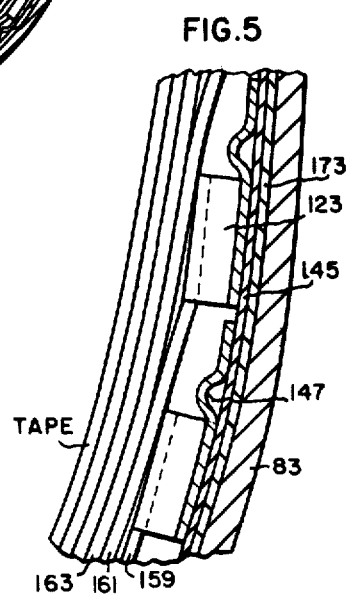
FIG. 5 is an enlarged view of the portion of FIG. 1 encircled by circle V.

The apparatus shown in the drawings includes a Fuel Capsule, Tape wound in spirals about the Fuel Capsule, a Capsule Support Spider, a Pulser and an Output Cable. The Fuel Capsule, Tape, and Spider are in a container formed by welding two cup-shaped halves 18 and 20 together.

The Capsule includes a plurality of radioactive units 21, 23, 25. Each unit includes an inner tube or sheath 27 within which there is a wire or bar 29 of radioactive material. The inner tube is enclosed within a middle tube or sheath 31. The tubes 31 are disposed in the partitions 33 of an outer can 35. Each of the tubes 27 and 31 and the partitions 33 are sealed by a plug 37, 39, 41 (FIG. 2) respectively welded to the associated tube.

Typically the fuel wire consists of "standard" purity plutonium 238 metal in the form of a small extruded wire approximately 1 inch long and about 0.022 inch in diameter in each of three cylindrical capsule liners or tubes 27. The inner or primary tube 27 is made of Ta-10W alloy and is capable of containing the pressure of the helium generated by the Pu 238 under the most severe credible accidents. The cylinder wall of each tube 27 is 0.030 inch thick and the end plug is 0.060 inch thick. Approximately 400% void volume is provided in the capsule to allow for ease of assembly and fuel form flexibility. The available data on materials compatibility indicate that there is no likelihood of damage from lack of compatibility of Ta-10W with Pu metal under the anticipated conditions of operation for the life of the generator. There is sound reason to believe that the generator would be safe under all credible thermal excursions including that caused by a high octane gasoline fire (1300° C) for periods up to five hours. Additional safety can be achieved by available flexibility which allows for use, in alternative practice of this invention, of a Zr-Pu fuel alloy or an additional encapsulation of Zr or Hf that would delay the dissolution attack of the container by forming a high melting point alloy with the plutonium at the interface.

*For brevity alloys are herein described in abbreviated form. The first chemical symbol describes the major component and the numbers before subsequent symbols the content of these components. Ta-10W is an alloy of tantalum-tungsten with 90% Ta and 10% W.

The Ta-10W tube 27 is protected from high-temperature oxidation by the Hastelloy "C" tube or sheath 31. Hastelloy C is selected because it has resistance to the corrosive effects of a broad spectrum of chemical reagents as well as resistance to oxidation at high temperatures. The Hastelloy sheath is 0.009 in. thick with 0.060 end plugs. Additional corrosion protection is obtained by a 0.001 inch coating of Pt over the Hastelloy which is provided to prevent reactions with the Ti outer can 35 during possible thermal excursions.

The three individual tubes 31 are contained in the outer can 35 of Ti to fix them in the required position and to facilitate the joining of the thermocouples to the heat source. Titanium is selected for ease and reliability of joining, high strength weight ratio, and because it has unique resistance to a broad spectrum of chemical reagents in which accidental immersion may be postulated. The use of Ti-0.2 Pd alloy, in alternative practice of this invention, allows the broadening of this spectrum to cover reducing reagents as well as oxidizing reagents.

The tube 27 is filled with helium or argon or other inert gas at about one atmosphere pressure and then the plug 37 is welded to its rim by electron-beam or tungsten-arc welding. The helium provides the thermal conductivity between the wire 29 and the Ta-10W wall. The tube 31 and the partitions 33 are evacuated and the plugs 39 and 41 sealed to their rims by electron-beam welding.

Alternative Fuel Capsules in the practice of this invention may include PuO2 as fuel. In addition platinum may replace the Hastelloy C alloy for the tube 31 where higher absorption of gamma rays is demanded.

The Fuel Capsule is supported by a Capsule Support Spider at each end. Each Spider (FIGS. 2 and 3) includes a T-plate or bracket 51, whose web 53 and cross member 55 have holes to reduce weight. Each web 53 has a wire support pin 57 at its end and the cross member 55 has like pins 59 and 61 at its ends. Capsule-support wires 63, 65, and 67, diverging from a center plate 68 (FIG. 2) to which they are secured at points that are about equally spaced, pass over the pins 57, 59 and 61 respectively and through spring tabs 69, 71 and 73 and are secured in grooves 75, 77, 79 respectively. The spring tabs 69, 71, 73 tension the wires 63, 65, 67. The tabs 69, 71, 73 are included to provide necessary damping and spring action against dynamic motion of the Fuel Capsule relative to the insulation and thermoelectric parts insuring impact and vibration protection. The cross members 55 of the T-plates 51 are each bolted to an angle 81 (FIG. 2) secured to the outside wall 83 of the generator. The plates 68 are secured to the ends of the Fuel Capsule.

Typically the T-plate 51 and the wires 63, 65, 67 may be composed of Ti-6Al-4V alloy. The wires 63, 65, 67 are of 0.005 inch diameter. The wires have an annealed tensile strength of about 130,000 pounds per square inch and are adequate to constrain the motion of the capsule. In addition to the mechanical considerations, the Ti-6Al-4V alloy is chosen for its low thermal conductivity in comparison with other high tensile strength wires. This assures a low heat loss through these wires.

The heat developed by the Fuel Capsule is converted into electricity by a thermoelectric pile embedded in the Tape. The thermoelectric pile includes a plurality of thermocouples 89 (FIG. 9) each composed of a pair of different wires 91 and 93 one electrically negative, or having excessive electrons, designated N and the other having excessive holes, designated P. The wires are connected at their ends in parallel in double pairs (FIGS. 8 and 9) to form hot junctions 92 at the Fuel Capsule and cold junctions 94 on the outside of the Tape. Typically, the wires 91 may be of CUPRON alloy and the wires 93 of TOPHEL alloy.

The Tape is composite and is made up of six layers (FIG. 8). There is a heat radiation reflecting layer 95 typically composed of Titanium-Zirconium foil. There are two layers 97 and 99 of thermoelectric cloth in which the wires 91 and 93 form the warp and electrical and thermal insulating threads 101 and 103, typically quartz threads, form the woof. The quartz threads 101 and 103 cross on both sides of the wires 91 and 93 at cross-over points 105 so that the wires 91 and 93 are thermally and electrically insulated from each other. There are layers 107, 109, 111 of thermally and electrically insulating cloth, typically quartz cloth, respectively between the radiation-reflecting layer 95 and the thermoelectric layer 97, the layer 97 and the layer 99, and the layer 99 and the reflecting layer 95 of the adjacent turn of Tape. The thermal radiation shield 95 of each layer of Tape extend beyond the thermoelectric cloth layers 101 and 103 and the insulating cloth layers 107, 109 and 111.

Each Tape includes a pair of ceramic connection tabs 121 and 123 (FIGS. 6, 9, 13A, 13B, 14A, 14B) one for the hot junction 92 and the other for the cold junction 94. The tabs 121 and 123 may be composed of a material such as alumina which is thermally conducting but electrically insulating. Each tab has a plurality of grooves 125 which are coated with a brazing compound 127, typically copper-silver. The layers 129 and 131 of copper and silver may be deposited on a titanium layer 133 (FIG. 14A) by evaporation or electroplating; the titanium is deposited by evaporation or fusion.

The ends of the thermocouple wires 91 and 93 extend freely from the thermocouple cloth. The junctions 92 and 94 are formed for each Tape by placing the ends in the grooves 125 coated with the layers 129, 131, 133 and heating the entire unit including the Tape and tabs 121 and 123 to the eutectic temperature of the brazing compound 127 which for copper-silver is 790° C. The compound 127 fuzes around the ends of the wires 91 and 93 (FIGS. 13B, 14B).

In view of the manner in which the wires 91 and 93 are woven into the cloth 97, 99 the proper placement of the wires in the required groove 127 is natural and presents no problem. The bottom of the alumina ceramic tabs 121 and 123 are brazed to thin tabs 141 and 143 of copper (FIGS. 1, 6, 9, 11, 12) which are then spot-brazed to a copper strap 145 (FIGS. 1, 2, 3, 5) which is later connected to the fuel capsule and to the external surface respectively of the generator. The copper tabs 141 and 143 are bent to compensate for thermal expansion and manufacturing tolerances which stress the Tape. The copper tabs 143 to which the ceramic is attached at the cold junctions 94 have small convolutions 147 (FIG. 1) to accommodate relative length changes in the tape during manufacturing and operations. This technique allows the ceramic 123 to essentially float with a thin copper piece which cannot stress it. The copper-silver eutectic does not wet the surface of the ceramic 121 or 123 and does not short out the junctions 92 or 94 by flowing over from junction to junction. It only wets the titanium 133 (FIG. 14A) and the thermocouple wires 91 and 93.

A plurality of Tapes 151, 153, 155, 157, 159, 161, 163 (FIG. 1) are wound spirally from a hot position contiguous to the Fuel Capsule to a position contiguous to the external container wall 83 of the generator. Each tape has ceramic terminals 121 and 123 on each side. The hot-junction ceramics 121 of the Tapes 151 through 163 are distributed around the periphery of the Fuel Capsule and the cold-junction ceramics 123 are distributed (spaced) along a portion of the half wall 18. The Tapes 151 to 163 start from positions spaced around the periphery of the Fuel Capsule and terminate at positions spaced along the inside of wall 83 and are interwound. The overlapping ends 95 of the radiation-shields 95 of the tapes form a generally frustoconical internal surface terminating at the wires 63 of the Capsule Support Spider. The interior of this surface is filled with sheets 171 of the titanium-zirconium thermal-radiation reflecting foil.

The hot junctions 92 of the Tape are connected in thermal interchange relationship with the Capsule through the copper strap 145 which is brazed to the Fuel Capsule. The cold junctions 94 are connected thermally to the wall 83 which is brazed to a connecting strap 173, in turn brazed to outer strap 145, in turn brazed to flexible connector or tab 143. The cold junction 94 of the end couple 175 (FIG. 15) on one side of the ceramic 123 connected to Tape 163 is electrically grounded to the wall 83. The cold junction of the end couple 177 on the opposite side is electrically connected to the cold junction of the adjacent end couple of the succeeding tape 161 through a strap 179 and the cold junction on the opposite side is likewise connected to the adjacent end couple of the next Tape 159 and so on, each strap 179 connecting the couples of a Tape, in series with the couples of the others. The cold junction of the end couple 181 of Tape 151 is connected to the output conductor 183 (FIG. 1) from the generator.

Typically each tape 151 through 163 has 424 thermocouple wires; these are connected to form 106 hot junctions and 107 cold junctions.

To assemble the generator the tapes 151 to 163 and the copper straps 145 are placed in a fixture which supports the tapes in the proper orientation with respect to the copper straps at both ends of the tapes. The copper tabs 141 and 143, which have been preattached to the ceramic tabs 121 and 123 to which the thermocouple ends have brazed, are joined to the copper heat transfer straps 145 located at both ends of the thermocouple tapes 151 through 163 by spot brazing with Cu-Ag alloy. The eight tapes are thereby combined into a single unified thermocouple assembly of the proper length and dimensions which can be entirely pretested before going on to the next step of assembly. The next step consists in attaching the tensile support wires 63, 65, 67 to the Fuel Capsule, placing the end thermal insulation 171 between the three support wires at each end, and affixing the tensile support wires to the support T-brackets 51 which have been pre-fixed to an assembly fixture. The assembly fixture is constructed so that the brackets 51 are held at the proper separation for insertion and fastening into the case 83. Care is taken to exert appropriate tension on the wires when they are fastened to the bracket. The insulation 171 (FIG. 2) is positioned within the tensile wires 63, 65, 67 and the fixture can be rotated about an axis passing through the center of the Fuel Capsule. Next the hot-junction end of the copper terminal thermocouple strap 145 is attached around the Fuel Capsule by first positioning the end of the terminal strap 145 into the groove provided in the Fuel Capsule and spot brazing the strap to the Capsule. The "cold" junction thermal joint is then attached to the copper strap 173 provided in half 18 of the container. This joint is made by spot brazing the ends of the copper straps 173 together with copper-silver eutectic alloy. The Fuel Capsule which is still affixed to its winding fixture is now rotated around its axis until the thermocouple tape assembly 151 through 163 is wound around the central axis, and the spider is then fastened to the brackets provided in the interior of the container. The hermetic lead 183 which is a thin flat strap, is attached to the electrical terminal on the thermocouple assembly, thus completing the electrical connection.

The unit, exclusive of the Pulser, is now placed in a high vacuum outgassing device and a vacuum provided where it will be outgassed at a temperature of 500° C until the pressure in the system is reduced to $10^{-6}$ millimeters of mercury. This drives off any residual water vapor, adsorbed gas or other contaminants which could, over the anticipated 10 year life, degrade the system and cause generator failure. The vacuum is broken with pure, dry argon after which the half 20 of the container is placed over the half 18. The assembled unit is then placed in a chill block fixture, evacuated to $10^{-6}$ mm of Hg, and electron-beam welded. This procedure ensures cleanliness and freedom from degrading contaminants which, as indicated above, may adversely affect the operation of the system over its lifetime.

The Pulser includes a hermetically sealed casing 201 mounted on the half 18 of the container adjacent to the point where the conductor 183 extends from the "hot" electrical terminal of the thermopile. Within the container 183 there is a pulse producing device 203 including solid state valves or transistors. Typically the Pulse producing device may be a free-running multivibrator with its impedances set to produce the pulses of the desired duration having the desired amplitudes and the desired on and off times. In a typical situation the pulse producer produces pulses of 2 millisecond durations at intervals of 500 milliseconds. The pulses have an amplitude of 6 milliamperes. The steady-state conduction of the device is about 3 microamperes.

The pulsing device has only one input terminal connected through a ceramic-to-metal feed-through connector 204 (FIG. 2), a conductor 205 and another ceramic-to-metal feedthrough connector 207, sealed through the half 18 of the container, to the conductor 183. The conductor 183 impresses about 6 volts negative on this input terminal. The opposite terminal of the pulser is grounded to the same ground as the grounded terminal of the thermopile. The pulsing device includes an output conductor 221 (FIG. 4) extending out of the container 201 and connected to a connector ring 223 to which it transmits the pluses produced.

The Pulser is molded in a generally rectangular mass 225 of transparent epoxy resin. The conductor 221 is embedded in this mass. The mass 225 includes a tubular opening 227 intermediate whose ends the ring 223 is molded. The opening 227 tapers slightly from both of its ends towards the ring 223.

The Output Cable includes a coiled conductor 231 typically of ELIGLOY alloy. The conductor 231 is enclosed in a flexible tube 233 preferably of silicone rubber which is enclosed in an insulating sheath 235 typically of silicone rubber. A stud 237 having a generally frusto-conical center portion 239 from which a screw 241 extends is secured in the end of the sheath 235. The conductor 231 is connected to the attenuated end 238 of the stud 237. The Output Cable also includes a connector nut 243. This nut 243 is slotted at one end 245 and carries an internal thread 247 at the other. There is a neck between the ends 245 and 247 on which an O-ring 249 is mounted. By turning the slotted head 245, the screw 241, frusto-conical portion 239, sheath 235 and the parts attached to it are pulled towards the ring 223 in one direction and the nut 243 and O-ring 249 are pulled in the opposite direction. The ring 223 has a tapered inner surface which is engaged in firm electrical contact by the portion 239. The O-ring seals the tapered hole 227 on one side and projections 251 on the outside of the sheath 235 seal the hole on the other side.

In the use of this apparatus the power generated by the thermopile energizes the Pulser which supplies pulses to actuate the heart.

Table 1 below shows the principal components included in the apparatus in accordance with this invention and the reasons for their selection:

TABLE I

| Item | Description | Reason for Selection |
| --- | --- | --- |
| Fuel (Preferred) | Pu-238 metal wire | Low surface radiation level. High energy density. Easily manufactured and shaped. Low manufacturing costs. |

TABLE I-continued

| Item | Description | Reason for Selection |
|---|---|---|
| (Alternate-1) | PuO$_2$ | Reasonable surface radiation levels for age groups representing vast majority of users. Highly inert. |
| (Alternate-2) | Pu-238 metal of special purity | Extra low surface radiation level. |
| Capsule Geometry | Triple Capsule | Low surface dose rate. Minimum thickness. Maximum strength. |
| Primary Fuel Capsule (Inner Unit 21) | Tantalum-10% tungsten alloy | Excellent compatibility with fuels. High strength at elevated temperatures to contain helium pressure. |
| Second Fuel Capsule (Middle Sheath 31) | Hastelloy "C" | High temperature oxidation resistance. Resistance to corrosion attack by industrial chemicals. Excellent high temperature compatibility with tantalum alloys. |
| Reaction Barrier | Platinum | Prevention of the development of low melting point phases between Hastelloy "C" and titanium. Excellent high temperature oxidation resistance. Excellent resistance to chemical attack. |
| Third Fuel Capsule (Cuter Can 35) | Titanium-0.2% Palladium alloy | Corrosion resistance to a broad range of chemical reagents. Ease of joining thermocouples. Excellent oxidation resistance. |
| Thermocouple Geometry | Spiral Wind | Ease of integration into insulation. Maximum diameter wire in small volume. High reliability. Provides for long length thus allowing greater diameter in a minimum of space. Allows for an all ceramic to metal system with high reliability. High surface area brazed joints allow for complete open assembly fixturing. Ease of manufacture and test. |
| Thermocouple Material | Cupron Special-Tophel Special | Ease of brazing and joining. Best figure of merits of state-of-the-art thermopile materials having good mechanical properties. Stability of metallurgical, mechanical, compositional and electrical properties. Readily available in desired wire diameters. Good mechanical properties. High reliability. Large L/A possible. No DC to DC converter required. |
| Thermal Radiation Insulation | Vacuum, Titanium-Zirconium Radiation Shields with Spiral Wind | High performance. Minimum thermal loss. Easily integrated into spiral wind. Self gettering of vacuum in case. |
| Electrical Insulation | Quartz cloth, Spiral Wind | Can be woven with thermocouple wires for low cost assembly in production. Spaces thermocouples for ease of assembly. Supports and cushions thermocouple wires. Can be outgassed at high temperatures. Separates irradiation shields. Stable operation in vacuum. |
| Outer Case and Anode | Titanium | Excellent compatibility with human tissue. Electrochemically inert. Corrosion resistance to body fluids. Good ductility and strength. Low density allows thicker, more reliable case. Excellent weldability when protected from the atmos- |

TABLE I-continued

| Item | Description | Reason for Selection |
| --- | --- | --- |
| | | phere. Good formability. Good bond strength to epoxy. Essentially pure material minimizes chances of metallurgical defects. |
| Case Closure Method | Electron-Beam Welding | Ease of weld fixturing. Small heat applied zone. Vacuum seal off at time of weld. |
| Potting Compound | Clear Epoxy | Excellent history of compatibility in body. Transparency allows surgeon to see final connection being made thereby assuring implantation reliability. Resistant to water swelling. Provides resilient mounting of electronic components and connections. May be autoclaved. Excellent joining to titanium. |
| Electrical Lead | Coiled Elgiloy Alloy | High strength-coil provides resiliency. High reliability bond on extended lift test. Excellent corrosion resistance. Excellent history of compatibility in body. |
| Lead Insulation | Silicon Rubber | Excellent resiliency. Excellent history of compatibility in body. Excellent electrical insulation. May be autoclaved, wide range of service temperatures. Resistant to water swelling. |
| Electrodes | Cathode "Chardack" electrode with 50 cm spiral Elgiloy electrode wire | Successful operating use. |
| Generator Interior Environment | Vacuum | Allows for minimum thermal loss. Allows for maximum life. Avoids gas pressure build up and leaks. Provides ultra-clean environment to prevent degradation. |
| Hot Junction Temperature | 200° C | Provides minimum of fuel loading at maximum efficiency point. Long life, High reliability. |
| Thermocouple Joining | Brazed Ceramic | High reliability. Ease of assembly. Large surface area, low resistivity joint. All ceramics and metal. Utilizes state-of-the-art brazes. Automatically interconnects circuit. Ease of check out. High shock resistant construction. Reinforced ceramic structure. Cushioned thermal connectors. |
| Capsule Support | Tensile wire (63, 65, 67) | High strength. Minimum thermal loss. Cushioned impact. Ease of assembly. Supports radiation shields. Easily joins to wall of capsule. High vibration and shock resistance. |
| Thermal Connections | Brazed Joints | Maximum reliability. Simplicity of assembly. Excellent heat transfer. High temp. outgassing capability. |

Typically, a heart pacer according to this invention has the properties outlined in the following Table II.

TABLE II

| Pulse Characteristics | |
| --- | --- |
| (a) Current | 4 to 10 milliamperes into 300 to 700 ohms paralleled by .25 microfarad and 1,000 ohm resistor |
| (b) Shape | 1.5 millisecond duration rectangular pulse |
| (c) Rate | |
| 1. Human | 70 plus or minus 5 per minute |
| 2. Animal | 120 plus or minus 5 per minute |
| Power Supply | |
| (a) Type | Metallic couples of Tophel |

TABLE II-continued

| | |
|---|---|
| (b) Circuitry | Special and Cupron Special Alloys Series- parallel |
| (c) Fuel | Plutonium 238 metal |
| (d) Total Power Output | 162 microwatts |
| Overall Characteristics | |
| (a) Size | 6 × 5 × 2.8 centimeters No radius smaller than .5 centimeters |
| (b) Weight | 97.5 grams |
| Specific Gravity | 1.4 (can be decreased with decrease in weight effected by removal of extra insulating tapes) |
| (c) External Radiation | Between 1.5 and 25 mrem/hr on surface of system |
| (d) Electrodes | |
| Cathode | Spiral Elgiloy Alloy wire |
| Anode | Titanium (Electrochemically Noble metal) 316L SS can also be used |
| (e) Operating Lifetime | |
| Human | 10 years objective - 20 probable |
| Animal | 5 years minimum |
| Environmental Conditions | |
| (a) Temperature | |
| 1. Ambient | 97° – 106° |
| 2. Surface | 109° F |

TABLE II-continued

| | |
|---|---|
| (b) Interface | Hermetically sealed, non-reactive container capable of operating in 100% humidity |
| (c) Shock | Considerably more than a 3 ft. drop to graphite surface can be tolerated |
| (d) Vibration | Minute man missile specifications. |

While a preferred embodiment has been disclosed herein, many modifications thereof are feasible. This invention then is not to be restricted except insofar as is necessitated by the prior art.

It is claimed:

1. A tape for a thermoelectric converter including cloth composed of threads interlaced with thermoelectric wires, said tape also including a layer of heat-radiation reflecting material extending over said cloth insulated from said wires.

2. The tape of claim 1 wherein the wires are of opposite thermoelectric polarity and are connected at the ends to form thermocouples.

* * * * *